US009907824B2

(12) United States Patent
Cifter et al.

(10) Patent No.: US 9,907,824 B2
(45) Date of Patent: *Mar. 6, 2018

(54) STABLE FORMULATIONS

(71) Applicant: MONTERO GIDA SANAYI VE TICARET A.S., Istanbul (TR)

(72) Inventors: Ümit Cifter, Istanbul (TR); Nazife Arabacioglu, Istanbul (TR); Özlem Toker, Istanbul (TR)

(*) Notice: Subject to any disclaimer, the term of this patent is extended or adjusted under 35 U.S.C. 154(b) by 80 days.

This patent is subject to a terminal disclaimer.

(21) Appl. No.: 14/436,169

(22) PCT Filed: Oct. 17, 2013

(86) PCT No.: PCT/EP2013/071741
§ 371 (c)(1),
(2) Date: Apr. 16, 2015

(87) PCT Pub. No.: WO2014/060525
PCT Pub. Date: Apr. 24, 2014

(65) Prior Publication Data
US 2015/0273003 A1 Oct. 1, 2015

(30) Foreign Application Priority Data
Oct. 18, 2012 (TR) ............... a 2012 12023

(51) Int. Cl.
A61K 36/25 (2006.01)
A61K 36/185 (2006.01)
A61K 9/00 (2006.01)
A61K 47/12 (2006.01)
A61K 47/26 (2006.01)

(52) U.S. Cl.
CPC ........... *A61K 36/25* (2013.01); *A61K 9/0095* (2013.01); *A61K 36/185* (2013.01); *A61K 47/12* (2013.01); *A61K 47/26* (2013.01); *A61K 2236/00* (2013.01)

(58) Field of Classification Search
CPC .................................................. A61K 36/00
See application file for complete search history.

(56) References Cited

U.S. PATENT DOCUMENTS

| | | | |
|---|---|---|---|
| 5,904,924 A | 5/1999 | Gaynor et al. | |
| 2004/0126441 A1 | 7/2004 | Pushpangadan et al. | |
| 2007/0014877 A1* | 1/2007 | Chatterjee et al. | ......... 424/725 |
| 2012/0309837 A1* | 12/2012 | Banerjee | ........... A61K 9/0078 514/630 |
| 2015/0273009 A1 | 10/2015 | Cifter et al. | |
| 2015/0290253 A1 | 10/2015 | Cifter et al. | |
| 2015/0290268 A1 | 10/2015 | Cifter et al. | |

FOREIGN PATENT DOCUMENTS

| | | |
|---|---|---|
| CH | 676931 A5 | 3/1991 |
| CN | 101204386 A * | 6/2008 |
| CN | 101637347 A | 2/2010 |
| CN | 101695563 A | 4/2010 |
| CN | 102100900 A | 6/2011 |
| CN | 102343077 A | 2/2012 |
| CN | 102641367 A * | 8/2012 |
| CN | 102698233 A | 10/2012 |
| DE | 4211745 A1 | 10/1993 |
| EP | 1520584 A1 | 4/2005 |
| EP | 1829548 A1 | 9/2007 |
| WO | WO-2009/011498 A1 | 1/2009 |
| WO | WO-2012/084075 A1 | 6/2012 |
| WO | WO-2014/060529 A1 | 4/2014 |
| WO | WO-2014/060533 A1 | 4/2014 |
| WO | WO-2014/060539 A1 | 4/2014 |

OTHER PUBLICATIONS

Fazio, Tolerance, safety and efficacy of Hedera helix extract in inflammatory bronchial diseases under clinical practice conditions: A prospective, open, multicentre postmarketing study in 9657 patients. Phytomedicine, (Jan. 2009) vol. 16, No. 1, pp. 17-24.*
Aimbire et al., "Effect of hydroalcoholic extract of Zingiber officinalis rhizomes on LPS-induced rat airway hyperreactivity and lung inflammation," Prostaglandins Leukot Essent Fatty Acids. 77(3-4):129-38 (2007).
Cohen et al., "Effectiveness of an herbal preparation containing echinacea, propolis, and vitamin C in preventing respiratory tract infections in children: a randomized, double-blind, placebo-controlled, multicenter study," Arch Pediatr Adolesc Med. 158(3):217-21 (2004).
Fazio et al., "Tolerance, safety and efficacy of Hedera helix extract in inflammatory bronchial diseases under clinical practice conditions: a prospective, open, multicentre postmarketing study in 9657 patients," Phytomedicine. 16(1):17-24 (2009).
Hofmann et al., "Efficacy of dry extract of ivy leaves in children with bronchial asthma—a review of randomized controlled trials," Phytomedicine. 10(2-3):213-20 (2003).
International Preliminary Report on Patentability for PCT Application No. PCT/EP2013/071766, dated Apr. 21, 2015 (6 pages).
International Preliminary Report on Patentability for PCT Application No. PCT/EP2013/071741, dated Apr. 21, 2015 (6 pages).
International Preliminary Report on Patentability for PCT Application No. PCT/EP2013/071750, dated Apr. 21, 2015 (7 pages).
International Preliminary Report on Patentability for PCT Application No. PCT/EP2013/071758, dated Apr. 21, 2015 (6 pages).
International Search Report and Written Opinion for PCT Application No. PCT/EP2013/071758, dated Jan. 23, 2014 (9 pages).
International Search Report and Written Opinion for PCT Application No. PCT/EP2013/071766, dated Jan. 23, 2014 (10 pages).
International Search Report and Written Opinion for PCT Application No. PCT/EP2013/071741, dated Jan. 23, 2014 (9 pages).
International Search Report and Written Opinion for PCT Application No. PCT/EP2013/071750, dated Jan. 23, 2014 (11 pages).

(Continued)

*Primary Examiner* — Qiuwen Mi
(74) *Attorney, Agent, or Firm* — Clark & Elbing LLP; Susan M. Michaud

(57) ABSTRACT

The present invention relates to a formulation comprising extracts of *Hedera helix* and *Pelargonium sidoides* for use in the treatment, prevention of, or the alleviation and/or elimination of the symptoms of various respiratory tract diseases, as well as a method for preparing this formulation.

20 Claims, No Drawings

(56) References Cited

OTHER PUBLICATIONS

Kemmerich et al., "Efficacy and tolerability of a fluid extract combination of thyme herb and ivy leaves and matched placebo in adults suffering from acute bronchitis with productive cough. A prospective, double-blind, placebo-controlled clinical trial," Arzneimittel Forschung./Drug Research. 56(9):652-60 (2006).

Matthys et al., "Efficacy and safety of an extract of Pelargonium sidoides (EPs 7630) in adults with acute bronchitis. A randomised, double-blind, placebo-controlled trial," Phytomedicine. 10(Suppl 4):7-17 (2003).

Matthys et al., "Pelargonium sidoides preparation (EPs 7630) in the treatment of acute bronchitis in adults and children," Phytomedicine. 14(Suppl 6):69-73 (2007).

Search Report and Written Opinion for Turkish Application No. TR201212043, dated Jul. 18, 2013 (18 pages).

Search and Written Opinion for Turkish Application No. TR201212044, dated May 14, 2013 (9 pages).

* cited by examiner

STABLE FORMULATIONS

FIELD OF INVENTION

The present invention relates to a novel formulation comprising *Hedera helix* extracts and *Pelargonium sidoides* extracts.

The present invention further relates to a method used for preparing a formulation comprising extracts of *Hedera helix* and *Pelargonium sidoides*, as well as to the use of this formulation in the treatment and prevention of various respiratory tract diseases, or in the alleviation and/or elimination of the symptoms thereof in mammalians, particularly in humans.

BACKGROUND OF INVENTION

In recent years, the use of various herbs and/or herbal medical products for the prevention and treatment of diseases and alleviating the effects thereof have been gradually increasing in all societies. Throughout the human history, there have been and still are attempts for treating many diseases (diabetes, jaundice, dyspnea, etc.) by using some herbs. According to the records of the World Heath Organization (WHO), a large proportion of the world's population (70-80%) make use of herbs for therapeutic or prophylactic purposes. Additionally, around 25% of prescription drugs in developed countries are composed of plant-based active agents (vinblastine, reserpine, quinine, aspirin, etc.).

Particularly following the end of the 1990s, the discovery of new areas of use for medical and aromatic herbs and the increasing demand for natural products have increased the use potential thereof day by day.

Herbal medical products have long been in use for the treatment or prophylaxis of respiratory diseases. In the treatment or prophylaxis of these diseases which are typically caused by viruses, bacteria, and/or fungi, it is quite significant both to eradicate these harmful organisms and to boost the immune system of the affected individual. This is because the immune system is comprised of processes providing protection against diseases, as well as recognizing and eliminating the pathogenic and tumor cells in a living being. The system scans the organism against any kind of foreign substances, entering or contacting the former, from viruses to parasitic worms of a wide variety, and distinguishes them from the organism's own healthy cells and tissues. The immune system can even distinguish substances with very similar features from each other to such an extent that even proteins having a different amino acid can be distinguished from the equivalents thereof. The function of the immune system is primarily to prevent harmful foreign substances from entering the respective organism, or upon entry, to retain the substances at the place of entry, or to prevent or delay their spreading therein.

*Hedera helix* (English Ivy) is one of the plant species used in the production of herbal products for the treatment and prevention of diseases, and/or for the alleviation and/or elimination of the symptoms thereof. *Hedera helix*, comprising saponins, phenol, and alkaloids, is known to be used for the treatment of cough, parasites, skin diseases, bronchitis, and chronic respiratory tract diseases. Various studies have been performed to demonstrate the effect of *Hedera helix* on said diseases. For instance, Erik van Wyk and Michael Wink stated in "Medicinal Plants of the World" that the expectorant action of *Hedera Helix* works by stimulating the "nervus vagus" in the stomach, causing a cough response. A study by S. Fazio et al. published in the January 2009 issue of "Phytomedicine" tested a dried leaf extract on 9657 patients with acute and chronic bronchitis, including children. Accordingly, it was observed that following one week, cough and chest pain disappeared or improved in 95% of patients.

*Pelargonium sidoides* (African Geranium, Umckaloabo) is a plant species widely used in the treatment and prevention of, or in the alleviation and/or elimination of the symptoms of cold and respiratory tract disease (pharyngitis, sinusitis, acute bronchitis, tonsillitis). It was determined to be effective in increasing the generation of natural killer cells and tumor necrosis factor alpha, and to enhance the release of interferon beta. *Pelargonium sidoides* has antiviral properties strengthening the immune system. It further has both antibacterial effects and antioxidative properties against some bacteria. Apart from that, it was also reported to boost the immune system of the respective organism and to have expectorant action by increasing the ciliary beat frequency of respiratory epithelial cells. In a multicenter study conducted by the Pneumology Department of a German University Hospital (2000) on acute bronchitis patients, including adults, children, and infants, it was determined that an extract of the roots of *Pelargonium sidoides* reduced the severity of the symptoms after 7 days treatment from 6.3 to 0.9 according to the average bronchitis severity score. A study published in "Acta Paediatrica" in April 2010, showed that preparations extracted from herbal roots were much more effective in the treatment of acute bronchitis as compared to placebo. A study group of children aged 6 to 18 years, taking the herbal extracts experienced less coughing, sputum, and bed rest times versus placebo. By assessing the results of four placebo-controlled clinic trials, the researchers at the Medical Center, the University of Pittsburgh, concluded that a standardized extract of *Pelargonium sidoides* showed a much better performance in alleviating the bronchitis symptoms versus placebo in a 7-day treatment period.

In prior art, there are many formulations, which comprises herbal agents or combinations of herbal agents, are disclosed. For example, WO2009/011498 A1 discloses a composition for the treatment of infection in the form of a syrup comprising *Pelargonium sidoides*; EP1829548 A1 discloses a composition comprising an extract of *Pelargonium sidoides*; KEMMERICH BERND at al.: "*Efficiency and tolerability of a fluid extract combination of thyme herb and ivy leaves and matched placebo in adults suffering from acute bronchitis with productive cough. A prospective, double-blind, placebo-controlled clinical trials*" (ARZNEIMITTEL FORSCHUNG. DRUG RESEARCH, Acv EDITO CANTOR VERLAG, AULENDORF, DE, vol. 56, no. 9, 1 Jan. 2006, pages 652-660) discloses the use of the combination of extracts of thyme herb and ivy leaves for the treatment of acute bronchitis; FAZIO S et al.: "*Tolerance, safety and efficacy of Hedera helix extract in inflammatory bronchial diseases under clinical practice conditions: A prospective, open, multicenter postmarketing study in 9657 patients*", (PHYTOMEDICINE, GUSTAV FISCHER VERLAG, STUTTGART, DE, vol. 16, no. 1, 2009, pages 17-24) discloses a composition in the form of a syrup comprising dried *Hedera helix* extract; HOFFMANN D et al.: "Efficacy of dry extract of ivy leaves in children with bronchial asthma—a review of randomized controlled trials", (PHYTOMEDICINE, GUSTAV FISCHER VERLAG, STUTTGART, DE, vol. 10, no. 2-3, 2003, pages 213-220) discloses a composition comprising dried ivy leaves for the treatment of chronic airway obstruction in children suffering from bronchial asthma. Although that there are many formulations which comprise herbal agents or combinations of herbal agents, the effects of a formulation comprising *Hedera helix* extracts and *Pelargonium sidoides* extracts are not known yet.

Products to be used for medical purposes have to incorporate the elements of quality, efficiency, and reliability. A product can be a "medical" product only by having these elements. In order for a product prepared from a herbal source to be a medical product, it has to be prepared from an efficient and standardized extract, to have established pharmacological, clinical outcomes and toxicological data, and a determined stability. Therefore, it bears great significance to have a good stability for a product, produced from herbal sources, to be used in the treatment and prevention of diseases, or in the alleviation and/or elimination of the symptoms thereof.

Physical, chemical, and microbiological factors play role in the stability of medicaments or other products prepared for medical purposes. The stability issue is not dependent on a simple cause only, but emerges as a result of many factors. Factors such as the interaction of active agents contained in a product, the interaction of excipients among themselves or with active agents, pH, light, humidity, and temperature are among many elements which may influence the stability of such products.

Until recently, the researchers deemed considerable importance on the chemical stability of pharmaceutical products rather than the physical stability thereof and conducted many studies accordingly. In many instances, however, they could —show how important the changes in the physical structures of products are for the product quality, and for the durability of the technologic, microbiologic, and biopharmaceutical properties thereof. Accordingly, it was shown that primarily the physical stability of a product has to be maintained in order to sustain its quality and other features thereof, and therefore ensuring the physical stability during the development of pharmaceutical products is as important as, or sometimes more important than ensuring the chemical stability thereof.

Additionally, the physical properties taken into account in the evaluation of the physical stability of a product, particularly the taste, scent, color, clarity, uniformity, etc. of a product, also considerably influence the patient compliance. For this reason, when a novel formulation is developed, besides aiming a formulation of good physical stability, the physical properties of this formulation should be made ideal to provide high patient compliance.

Having said that, it is quite difficult to ensure the requirements mentioned above in the formulations comprising herbal agents. Due to some characteristic chemical, biological, and physical properties of herbal agents incorporated in a formulation, some difficulties are experienced in obtaining a formulation comprising such substances, and having both good physical stability and ideal features in terms of patient compliance.

The physical properties and the physical stability of a formulation are influenced directly from the characteristic properties of herbal agents contained therein. Some aspects of herbal agents contained in a formulation, such as having a bad taste, a bad scent, a bad color, and similar physical properties, becoming easily oxidized, and providing a suitable medium for the reproduction of microorganisms negatively influence the physical properties and physical stability of that formulation. Additionally, in case a formulation comprises a combination of herbal agents, a correct selection of the herbal agents bears great importance since more than one herbal agent present in the same formulation are capable to mutually affect their respective properties.

Under the light of the foregoing, it would be desirable to provide a formulation, as well as a process for the preparation of this formulation, comprising combinations of herbal agents, being capable to retain the physical stability for a long time, and having ideal physical properties in terms of patient compliance.

In detail, there is a need in the relevant art to a formulation comprising extracts of *Hedera helix* and *Pelargonium sidoides* and having ideal physical properties to ensure high patient compliance and good physical stability, as well as to a method for preparing this formulation, which is simple, cost-efficient and time-saving.

OBJECT OF INVENTION

The main object of the present invention is to provide a novel formulation comprising extracts of *Hedera helix* and *Pelargonium sidoides*, overcoming the problems referred to above, and having advantages over the prior art formulations.

According to this main object, the formulations according to the present invention are convenient for the treatment, prevention of, or the alleviation and/or elimination of the symptoms of various respiratory tract diseases.

Another object of the present invention is to provide a formulation comprising extract of *Hedera helix* and extract of *Pelargonium sidoides*, which has improved physical stability.

A further object of the present invention is to provide a formulation comprising extract of *Hedera helix* and extract of *Pelargonium sidoides*, which has increased quality, reliability, and shelf life as a result of an improved physical stability.

Another object of the present invention is to provide a formulation comprising extract of *Hedera helix* and extract of *Pelargonium sidoides*, which both maintains the physical stability and has improved physical properties as a result of using suitable excipients.

A further object of the present invention is to provide a simple, cost-efficient, and time-saving process for preparing a formulation comprising extract of *Hedera helix* and extract of *Pelargonium sidoides*.

DESCRIPTION OF INVENTION

The maintenance of the physical stability of a pharmaceutical product can be ensured if no change occurs in the physical structure of that product. Therefore, the change in some physical properties of the product during a formulation development process is determined and it is assessed whether the physical stability is maintained. Properties such as the color, scent, taste, pH, clarity, viscosity, uniformity, density, etc. among the physical properties of a pharmaceutical product are the basic physical properties playing role in an evaluation of the physical stability of that product.

In the physical stability studies conducted during the development of a formulation comprising *Hedera helix* extract for use in medicine, it was surprisingly found that adding extract of another herbal agent, namely *Pelargonium sidoides*, into the formulation, improved the physical stability of the product, and thus, the physical properties such as the color, scent, taste, pH, clarity, viscosity, uniformity, and the density thereof at the time the formulation was prepared were maintained for a longer time such that the physical stability was maintained as well.

In other words, it was found that the physical properties such as the color, scent, taste, density, clarity, homogeneity, viscosity, and the pH which are taken into account while the physical stability of a formulation comprising extracts of *Hedera helix* and *Pelargonium sidoides* is evaluated remained unchanged for a longer time as compared to a formulation comprising the *Hedera helix* extract only.

Accordingly, the present invention provides a formulation with good physical stability, comprising extract of *Hedera helix* and extract of *Pelargonium sidoides*.

According to another aspect of the present invention, the percentage amount of the *Hedera helix* extract is between 0.05% and 20% (w/v), preferably between 0.1% and 15% (w/v), and more preferably between 0.25% and 10% (w/v) based on the total volume of the formulation, whereas the percentage amount of *Pelargonium sidoides* between 0.05% and 30% (w/v), preferably between 0.1% and 20% (w/v), and more preferably between 0.2% and 15% (w/v) based on the total volume of the formulation. Here, the percentage amount of the *Hedera helix* extract is the gram-based amount of the *Hedera helix* extract per 100 ml of formulation, whereas the percentage amount of the *Pelargonium sidoides* extract is the gram-based amount of the *Pelargonium sidoides* extract per 100 ml of formulation When the *Hedera helix* extract and the *Pelargonium sidoides* extract were used at a specific weight ratio in the formulation according to the present invention, i.e. when the weight ratio of the *Hedera helix* extract to the *Pelargonium sidoides* extract was in the range of 1:0.1 to 1:45, it was surprisingly observed that this had a synergistic effect on the physical stability of said formulation. Thus, by providing an improved physical stability; the quality, reliability, and the shelf life of the formulation according to the present invention are increased.

More specifically, the present invention provides a formulation comprising extracts of *Hedera helix* and *Pelargonium sidoides*, wherein the weight ratio of the *Hedera helix* extract to the *Pelargonium sidoides* extract is between 1:0.1 and 1:45.

According to the present invention, the weight ratio of the *Hedera helix* extract to the *Pelargonium sidoides* extract in said formulation is between 1:0.1 and 1:45, e.g. between 1:0.1 and 1:42.5; between 1:0.1 and 1:40; between 1:0.1 and 1:37.5; between 1:0.1 and 1:35; between 1:0.1 and 1:32.5; between 1:0.1 and 1:30; between 1:0.1 and 1:27.5; between 1:0.1 and 1:25; between 1:0.1 and 1:22.5; between 1:0.1 and 1:20; between 1:0.1 and 1:17.5; between 1:0.1 and 1:15; between 1:0.1 and 1:12.5; between 1:0.1 and 1:10; between 1:0.3 and 1:42.5; between 1:0.3 and 1:40; between 1:0.3 and 1:37.5; between 1:0.3 and 1:35; between 1:0.3 and 1:32.5; between 1:0.3 and 1:30; between 1:0.3 and 1:27.5; between 1:0.3 and 1:25; between 1:0.3 and 1:22.5; between 1:0.3 and 1:20; between 1:0.3 and 1:17.5; between 1:0.3 and 1:15; between 1:0.3 and 1:12.5; between 1:0.3 and 1:10; between 1:0.5 and 1:42.5; between 1:0.5 and 1:40; between 1:0.5 and 1:37.5; between 1:0.5 and 1:35; between 1:0.5 and 1:32.5; between 1:0.5 and 1:30; between 1:0.5 and 1:27.5; between 1:0.5 and 1:25; between 1:0.5 and 1:22.5; between 1:0.5 and 1:20; between 1:0.5 and 1:17.5; between 1:0.5 and 1:15; between 1:0.5 and 1:12.5; between 1:0.5 and 1:10; between 1:0.8 and 1:42.5; between 1:0.8 and 1:40; between 1:0.8 and 1:37.5; between 1:0.8 and 1:35; between 1:0.8 and 1:32.5; between 1:0.8 and 1:30; between 1:0.8 and 1:27.5; between 1:0.8 and 1:25; between 1:0.8 and 1:22.5; between 1:0.8 and 1:20; between 1:0.8 and 1:17.5; between 1:0.8 and 1:15; between 1:0.8 and 1:12.5; between 1:0.8 and 1:10; between 1:1 and 1:42.5; between 1:1 and 1:40; between 1:1 and 1:37.5; between 1:1 and 1:35; between 1:1 and 1:32.5; between 1:1 and 1:30; between 1:1 and 1:27.5; between 1:1 and 1:25; between 1:1 and 1:22.5; between 1:1 and 1:20; between 1:1 and 1:17.5; between 1:1 and 1:15; between 1:1 and 1:12.5; between 1:1 and 1:10; between 1:1.2 and 1:42.5; between 1:1.2 and 1:40; between 1:1.2 and 1:37.5; between 1:1.2 and 1:35; between 1:1.2 and 1:32.5; between 1:1.2 and 1:30; between 1:1.2 and 1:27.5; between 1:1.2 and 1:25; between 1:1.2 and 1:22.5; between 1:1.2 and 1:20; between 1:1.2 and 1:17.5; between 1:1.2 and 1:15; between 1:1.2 and 1:12.5; between 1:1.2 and 1:10; between 1:1.5 and 1:42.5; between 1:1.5 and 1:40; between 1:1.5 and 1:37.5; between 1:1.5 and 1:35; between 1:1.5 and 1:32.5; between 1:1.5 and 1:30; between 1:1.5 and 1:22.5; between 1:1.5 and 1:20; between 1:1.5 and 1:17.5; between 1:1.5 and 1:15; between 1:1.5 and 1:12.5; and between 1:1.5 and 1:10.

According to a preferred aspect of the present invention, the weight ratio of the *Hedera helix* extract to the *Pelargonium sidoides* extract in the subject formulation is between 1:0.25 and 1:25, e.g. between 1:0.25 and 1:24; between 1:0.25 and 1:22; between 1:0.25 and 1:20; between 1:0.25 and 1:18; between 1:0.25 and 1:16; between 1:0.25 and 1:14; between 1:0.25 and 1:12; between 1:0.25 and 1:10; between 1:0.25 and 1:8; between 1:0.25 and 1:6, between 1:0.25 and 1:4; between 1:0.4 and 1:24; between 1:0.4 and 1:22; between 1:0.4 and 1:20; between 1:0.4 and 1:18; between 1:0.4 and 1:16; between 1:0.4 and 1:14; between 1:0.4 and 1:12; between 1:0.4 and 1:10; between 1:0.4 and 1:8; between 1:0.4 and 1:6, between 1:0.4 and 1:4; between 1:0.7 and 1:24; between 1:0.7 and 1:22; between 1:0.7 and 1:20; between 1:0.7 and 1:18; between 1:0.7 and 1:16; between 1:0.7 and 1:14; between 1:0.7 and 1:12; between 1:0.7 and 1:10; between 1:0.7 and 1:8; between 1:0.7 and 1:6, between 1:0.7 and 1:4; between 1:0.9 and 1:24; between 1:0.9 and 1:22; between 1:0.9 and 1:20; between 1:0.9 and 1:18; between 1:0.9 and 1:16; between 1:0.9 and 1:14; between 1:0.9 and 1:12; between 1:0.9 and 1:10; between 1:0.9 and 1:8; between 1:0.9 and 1:6, between 1:0.9 and 1:4; between 1:1.1 and 1:24; between 1:1.1 and 1:22; between 1:1.1 and 1:20; between 1:1.1 and 1:18; between 1:1.1 and 1:16; between 1:1.1 and 1:14; between 1:1.1 and 1:12; between 1:1.1 and 1:10; between 1:1.1 and 1:8; between 1:1.1 and 1:6, between 1:1.1 and 1:4; between 1:1.3 and 1:24; between 1:1.3 and 1:22; between 1:1.3 and 1:20; between 1:1.3 and 1:18; between 1:1.3 and 1:16; between 1:1.3 and 1:14; between 1:1.3 and 1:12; between 1:1.3 and 1:10; between 1:1.3 and 1:8; between 1:1.3 and 1:6, between 1:1.3 and 1:4; between 1:1.5 and 1:24; between 1:1.5 and 1:22; between 1:1.5 and 1:20; between 1:1.5 and 1:18; between 1:1.5 and 1:16; between 1:1.5 and 1:14; between 1:1.5 and 1:12; between 1:1.5 and 1:10; between 1:1.5 and 1:8; between 1:1.5 and 1:6, and between 1:1.5 and 1:4.

According to another preferred aspect of the present invention, the weight ratio of the *Hedera helix* extract to the *Pelargonium sidoides* extract in said formulation is between 1:0.5 and 1:15, e.g. between 1:0.5 and 1:14; between 1:0.5 and 1:13; between 1:0.5 and 1:12; between 1:0.5 and 1:11; between 1:0.5 and 1:10; between 1:0.5 and 1:9; between 1:0.5 and 1:8; between 1:0.5 and 1:7; between 1:0.5 and 1:6; between 1:0.5 and 1:5; between 1:0.5 and 1:4; between 1:0.5 and 1:3; between 1:0.5 and 1:2; between 1:0.6 and 1:14; between 1:0.6 and 1:13; between 1:0.6 and 1:12; between 1:0.6 and 1:11; between 1:0.6 and 1:10; between 1:0.6 and 1:9; between 1:0.6 and 1:8; between 1:0.6 and 1:7; between 1:0.6 and 1:6; between 1:0.6 and 1:5; between 1:0.6 and 1:4; between 1:0.6 and 1:3; between 1:0.6 and 1:2; between 1:0.7 and 1:14; between 1:0.7 and 1:13; between 1:0.7 and 1:12;

between 1:0.7 and 1:11; between 1:0.7 and 1:10; between 1:0.7 and 1:9; between 1:0.7 and 1:8; between 1:0.7 and 1:7; between 1:0.7 and 1:6; between 1:0.7 and 1:5; between 1:0.7 and 1:4; between 1:0.7 and 1:3; between 1:0.7 and 1:2; between 1:0.8 and 1:14; between 1:0.8 and 1:13; between 1:0.8 and 1:12; between 1:0.8 and 1:11; between 1:0.8 and 1:10; between 1:0.8 and 1:9; between 1:0.8 and 1:8; between 1:0.8 and 1:7; between 1:0.8 and 1:6; between 1:0.8 and 1:5; between 1:0.8 and 1:4; between 1:0.8 and 1:3; between 1:0.8 and 1:2; between 1:0.9 and 1:14; between 1:0.9 and 1:13; between 1:0.9 and 1:12; between 1:0.9 and 1:11; between 1:0.9 and 1:10; between 1:0.9 and 1:9; between 1:0.9 and 1:8; between 1:0.9 and 1:7; between 1:0.9 and 1:6; between 1:0.9 and 1:5; between 1:0.9 and 1:4; between 1:0.9 and 1:3; between 1:0.9 and 1:2; between 1:1 and 1:14; between 1:1 and 1:13; between 1:1 and 1:12; between 1:1 and 1:11; between 1:1 and 1:10; between 1:1 and 1:9; between 1:1 and 1:8; between 1:1 and 1:7; between 1:1 and 1:6; between 1:1 and 1:5; between 1:1 and 1:4; between 1:1 and 1:3; between 1:1 and 1:2; between 1:1.1 and 1:14; between 1:1.1 and 1:13; between 1:1.1 and 1:12; between 1:1.1 and 1:11; between 1:1.1 and 1:10; between 1:1.1 and 1:9; between 1:1.1 and 1:8; between 1:1.1 and 1:7; between 1:1.1 and 1:6; between 1:1.1 and 1:5; between 1:1.1 and 1:4; between 1:1.1 and 1:3; between 1:1.1 and 1:2; between 1:1.2 and 1:14; between 1:1.2 and 1:13; between 1:1.2 and 1:12; between 1:1.2 and 1:11; between 1:1.2 and 1:10; between 1:1.2 and 1:9; between 1:1.2 and 1:8; between 1:1.2 and 1:7; between 1:1.2 and 1:6; between 1:1.2 and 1:5; between 1:1.2 and 1:4; between 1:1.2 and 1:3; between 1:1.2 and 1:2; between 1:1.3 and 1:14; between 1:1.3 and 1:13; between 1:1.3 and 1:12; between 1:1.3 and 1:11; between 1:1.3 and 1:10; between 1:1.3 and 1:9; between 1:1.3 and 1:8; between 1:1.3 and 1:7; between 1:1.3 and 1:6; between 1:1.3 and 1:5; between 1:1.3 and 1:4; between 1:1.3 and 1:3; between 1:1.3 and 1:2; between 1:1.4 and 1:14; between 1:1.4 and 1:13; between 1:1.4 and 1:12; between 1:1.4 and 1:11; between 1:1.4 and 1:10; between 1:1.4 and 1:9; between 1:1.4 and 1:8; between 1:1.4 and 1:7; between 1:1.4 and 1:6; between 1:1.4 and 1:5; between 1:1.4 and 1:4; between 1:1.4 and 1:3; between 1:1.4 and 1:2; between 1:1.5 and 1:14; between 1:1.5 and 1:13; between 1:1.5 and 1:12; between 1:1.5 and 1:11; between 1:1.5 and 1:10; between 1:1.5 and 1:9; between 1:1.5 and 1:8; between 1:1.5 and 1:7; between 1:1.5 and 1:6; between 1:1.5 and 1:5; between 1:1.5 and 1:4; between 1:1.5 and 1:3; and between 1:1.5 and 1:2.

In another aspect, the formulation according to the present invention comprising *Hedera helix* extract and *Pelargonium sidoides* extract may be administered by oral, parenteral, ocular, nasal, buccal, sublingual, and topical route.

In a preferred aspect of the present invention, said formulation is for oral administration. On the other hand, infants, children, elders or those individuals having difficulty in swallowing can not easily use solid oral dosage forms. For this reason, as well as to ensure high patient compliance and successful treatment course, the formulation according to the present invention is preferably presented in a liquid oral dosage form and particularly in the form of a syrup.

In the formulations according to the present invention comprising the above indicated amounts of the *Hedera helix* extract and the *Pelargonium sidoides* extract, no changes occurred in the properties including the taste, scent, appearance, viscosity, pH, and clarity thereof, for a relatively longer time period, as compared to those formulations comprising the *Hedera helix* extract only, and thus a more prolonged physical stability was provided.

In a further aspect of the present invention, said formulation further comprises at least one excipient besides the *Hedera helix* extract and the *Pelargonium sidoides* extract as the active agents. Accordingly, the formulation according to the present invention comprises at least one pharmaceutically acceptable excipient selected from the group comprising fillers, solvents, pH regulating agents, sweeteners, aromatic agents and preservatives.

It is probable that excipient(s) contained in a formulation interact(s) with active agents and/or among themselves, such that the properties, efficiency, and/or stability of the formulation is influenced in a positive or negative manner. For this reason, the selection of the excipients for a formulation according to the present invention has to be made very carefully and by keeping in mind the object of the present invention.

Suitable fillers which may be contained in a formulation according to the present invention are selected from a group comprising, but not limited to, sucrose, sorbitol, xylitol, dextrose, fructose, maltitole, sugar potassium, aspartame, saccharine, saccharine sodium, spray dried or anhydrous lactose, mannitol, starch, cellulose (preferably microcrystalline cellulose), and the mixtures thereof; wherein the preferred filler is sorbitol.

Fillers are used in oral liquid formulations as a dispersing medium. Fillers may also be used for setting the concentration and improving the reproducibility of a formulation. In oral liquid formulations, these excipients are used preferably in solution form.

Sorbitol has also some physical and chemical properties which make it ideal to be selected as a suitable filler for use in the present invention. It is chemically inactive and is compatible with many other excipients. In addition, it is easily dissolvable in water and contributes to maintaining the stability of a formulation by increasing the viscosity thereof. Besides all these features, sorbitol is also used as a sweetener in pharmaceutical formulations.

In a formulation according to the present invention, it was found that when sorbitol was contained in an amount between 1% and 60% (w/v) based on the total volume of the formulation, it contributed both to improving the taste of the formulation, and to the prevention of crystallization thereof so that the physical stability and particularly the homogeneity and the clarity of the formulation was maintained. The percentage amount of sorbitol contained in a formulation according to the present invention is preferably between 5% and 30% (w/v) and more preferably between 10% and 25% (w/v), based on the total volume of the formulation.

Suitable pH regulating agents which may be contained in a formulation according to the present invention are selected from a group comprising, but not limited to, ascorbic acid, acetic acid, tartaric acid, citric acid, sodium citrate, potassium citrate, sodium phosphate, tricalcium phosphate, calcium carbonate, sodium bicarbonate, calcium phosphates, carbonated calcium phosphates, magnesium hydroxide and the hydrates thereof and the mixtures thereof; wherein the preferred pH regulating agents are citric acid monohydrate and sodium citrate dihydrate.

According to the present invention, it was observed that setting the weight ratio of sodium citrate dihydrate to citric acid monohydrate contained in said formulation at 1:2 and thus keeping the pH at an acidic level contributed to improving the taste of the formulation and to maintaining the physical stability of the formulation, based on a constant pH. The percentage amount of citric acid monohydrate in said formulation is between 0.01% and 1% (w/v), preferably between 0.02% and 0.5% (w/v), more preferably between 0.03% and 0.2% based on the total volume of the formulation, whereas the percentage amount of sodium citrate dihydrate is between 0.005% and 0.5% (w/v), preferably between 0.01% and 0.25%, and more preferably between 0.015% and 0.1% on the same basis. The pH of the formulation according to the present invention is between 2 and 6.5, preferably between 3 and 6, and more preferably between 3.5 and 5.5.

Suitable preservatives which may be contained in a formulation according to the present invention are selected from a group comprising, but not limited to, methylparaben and propylparaben and the salts thereof (e.g. sodium, potassium), sodium benzoate, citric acid, benzoic acid, butylated hydroxytoluene and butylated hydroxyanisole, and the mixtures thereof.

Suprisingly, it was found that when the above indicated percentages of *Pelargonium sidoides* extract were added to a formulation according to the present invention, the need to include a preservative in said formulation was avoided due to the characteristic features of *Pelargonium sidoides*, particularly the antibacterial, antiviral, and/or antioxidative features of the same. Thus, when a formulation according to the present invention comprises the above indicated percentages of *Pelargonium sidoides* extract, the physical stability thereof can be maintained for a longer time without containing a preservative and a more natural formulation can be obtained as compared to the formulation comprising a preservative.

Suitable aromatic agents which may be contained in a formulation according to the present invention are selected from a group comprising, but not limited to, fruit aromas such as of orange, cherry, strawberry, banana, sourcherry, lemon; aromas of cardamom, anis, mint, menthol, eucalyptus, vanillin, and ethyl vanillin and the mixtures thereof, wherein the preferred aromatic agent is eucalyptus.

When eucalyptus was used as an aromatic agent as said above, it was observed that eucalyptus provided a supportive effect on the action of the formulation based on the refreshing and smoothening effects of eucalyptus scent, and that patients receiving this formulations experienced an instant relief as well as a reduction in the symptoms, and thus it helped them to feel better in a relatively short time. Based on said effect of a formulation according to the present invention comprising eucalyptus as an aromatic agent, it was further observed that the formulation increased patient compliance and that the process in which the patients using this formulation complied with the treatment was accelerated.

The percentage amount of eucalyptus used as an aromatic agent according to the present invention is preferably between 0.01% and 5% (w/v) and preferably between 0.03% and 3% (w/v), more preferably between 0.05% and 2% based on the total volume of the formulation.

Suitable sweeteners which may be contained in a formulation according to the present invention are selected from a group comprising, but not limited to, sucralose, ammonium glycyrrhizinate, acesulfame-K, aspartame, saccharine or sodium and calcium salts of saccharine, sodium cyclamate, sucrose, fructose, glucose, sorbitol and the mixtures thereof. The percentage amount of a sweetener contained in a formulation according to the present invention is between 0.005% and 20% (w/v), preferably between 0.005% and 15% (w/v) and more preferably between 0.005% and 10% (w/v), based on the total volume of the formulation.

Suitable solvents which may be contained in a formulation according to the present invention are selected from a group comprising, but not limited to, propylene glycol, glycerin, water, ethanol, isopropyl alcohol and similar water-soluble polar and water-insoluble non-polar solvents, or the mixture thereof. In order to prepare a formulation according to the present invention in an ideal manner, at least 5% and preferably at least 15% thereof has to be comprised of a solvent.

In a further aspect of the present invention, beside the *Hedera helix* extract and the *Pelargonium sidoides* extract contained as active agents in said formulation, the formulation may further comprise the extracts of at least one of the following plants, which are known to be useful in the treatment, prevention of, or in the alleviation and/or elimination of the symptoms of various respiratory tract diseases and in boosting the immune system: *Allium sativum, Juglans regia, Echinacea angustifolia, Echinacea atrorubens, Echinacea laevigata, Echinacea pallida, Echinacea paradoxa, Echinacea purpurea, Echinacea sanguinea, Echinacea simulata, Echinacea tennesseensis, Propolis, Glycyrrhiza glabra, Zingiber officinale, Viola tricolor, Carduus marianus, Uncaria tomantosa, Codonopsis pilosula, Schisandra chinensis, Gynostemma pentaphyllum, Ginseng* root, *Eleutherococcus senticosus, Pseudostellaria heterophylla, Withania somnifera, Pfaffia paniculata, Lepidium meyenii, Oplopanax horridus, Angelica sinensis, Panax notoginseng, Thymus citriodorus, Thymus herba-barona, Thymus pseudolanuginosus, Thymus serpyllum, Thymus vulgaris, Sambucus nigra, Tussilago farfara, Pimpinella anisum, Polypodium vulgare, Pinellia ternata, Citrus reticulata, Melissa officinalis, Primula veris, Lobelia* species, *Mullein* species, *Mentha piperita*.

According to the present invention, in addition to the *Hedera helix* extract and *Pelargonium sidoides* extract contained in said formulation as active agents, the formulation comprises at least one of the extracts more preferably of *Echinacea purpurea*, Propolis, *Glycyrrhiza glabra, Zingiber officinale* ye *Ginseng* root (preferably *Panax ginseng*)

The formulation according to the present invention can be used as a pharmaceutical and/or phytotherapeutic formulation, or alternatively as a food supplement.

According to the present invention, the extract of *Hedera helix* can be obtained from the shell, leaf, flower, root or from the seed of *Hedera helix*. Similarly, the extract of *Pelargonium sidoides* can be obtained from the shell, leaf, flower, root or from the seed of *Pelargonium sidoides*.

All extracts according to the present invention are obtained using methods of the prior art.

In another aspect, the present invention provides a formulation used for the treatment, prevention of, and/or in the alleviation of the effects of parasitic diseases, skin diseases, acute and chronic respiratory tract infections, cold, pharyngitis, angina, sinusitis, acute bronchitis, tonsillitis, bronchial asthma, chronic obstructive pulmonary disease, acute and chronic airway inflammation, lower and upper respiratory tract infections, acute and chronic inflammatory bronchial diseases, infections of the ear, nose, and throat, bacterial and viral other respiratory tract diseases. Additionally, the formulation according to the present invention can be used in the alleviation and/or elimination of the symptoms of said diseases, in boosting the immune system, in alleviating the symptoms like cough and the sore throat, as well as be used as an expectorant, as an anti-inflammatory agent, antibacterial agent and antiviral agent.

A formulation according to the present invention preferably in a liquid oral dosage form comprising herbal agents and having an improved physical stability comprises the followings:

a. 0.05% to 20% by weight of *Hedera helix* extract,
b. 0.05% to 30% by weight of *Pelargonium sidoides* extract,
c. 1% to 60% by weight of propylene glycol,
d. 25% to 50% by weight of glycerin,
e. 0.01% to 1% by weight of citric acid monohydrate,
f. 0.005% to 0.5% by weight of sodium citrate dihydrate,
g. 1% to 60% by weight of sorbitol,
h. 0.01% to 2% by weight of sucralose,
i. 0.01% to 10% by weight of ammonium glycyrrhizinate,
j. 0.5% to 30% by weight of ethanol,
k. 0.01% to 5% by weight of eucalyptus,
l. sufficient quantity of water to give a total volume of 100 ml.

In a preferred aspect of the present invention, the aforesaid formulation formulated comprises the followings:
a. 0.1% to 15% by weight of *Hedera helix* extract,
b. 0.1% to 20% by weight of *Pelargonium sidoides* extract,
c. 5% to 30% by weight of propylene glycol,
d. 25% to 50% by weight of glycerin,
e. 0.02% to 0.5% by weight of citric acid monohydrate,
f. 0.01% to 0.25% by weight of sodium citrate dihydrate,
g. 5% to 30% by weight of sorbitol,
h. 0.01% to 2% by weight of sucralose,
i. 0.01% to 10% by weight of ammonium glycyrrhizinate,
j. 0.5% to 30% by weight of ethanol,
k. 0.03% to 3% by weight of eucalyptus,
l. sufficient quantity of water to give a total volume of 100 ml.

In another preferred aspect of the present invention, the aforesaid formulation comprises the followings:
a. 0.25% to 10% by weight of *Hedera helix* extract,
b. 0.2% to 15% by weight of *Pelargonium sidoides* extract,
c. 10% to 30% by weight of propylene glycol,
d. 25% to 50% by weight of glycerin,
e. 0.03% to 0.2% by weight of citric acid monohydrate,
f. 0.015% to 0.1% by weight of sodium citrate dihydrate,
g. 10% to 25% by weight of sorbitol,
h. 0.01% to 2% by weight of sucralose,
i. 0.01% to 10% by weight of ammonium glycyrrhizinate,
j. 0.5% to 30% by weight of ethanol,
k. 0.05% to 2% by weight of eucalyptus,
l. sufficient quantity of water to give a total volume of 100 ml.

According to the present invention, the percentage amount by weight of an ingredient contained in the formulation represents a gram-based amount of that ingredient per 100 ml of formulation.

According to another object of the present invention, a preferred process of the present invention for preparing a formulation comprises the following steps:
a. all solvents are added to a container where production is to be made and are stirred until a homogeneous mixture is obtained (mixture A),
b. inactive ingredients are added to the container containing the mixture A and are stirred until a homogeneous mixture is obtained (mixture B),
c. *Hedera helix* extract and *Pelargonium sidoides* extract, which are the herbal active agents, are added respectively to mixture B obtained in the preceding step and are stirred until a homogeneous mixture is obtained (mixture C),
d. the mixture C obtained is converted into a suitable dosage form and filled into packages.

Another preferred process of the present invention for preparing a formulation according to the present invention which is preferably in a liquid oral dosage form comprises the following steps:
a. all solvents are added to a production container and are stirred until a homogeneous mixture is obtained (mixture A),
b. inactive ingredients are added to the container containing the mixture A and are stirred until a homogeneous mixture is obtained (mixture B),
c. *Hedera helix* extract and *Pelargonium sidoides* extract, which are the active agents, are added respectively to mixture B obtained in the preceding step and are stirred until a homogeneous mixture is obtained (mixture C),
d. the resulting mixture C is filtered and is let to settle,
e. following the settling period, the resulting final product is filled into suitable bottles.

During the production processes described above, the homogenizer and the mixer used are run at high rpm and the stirring process is proceeded until a homogeneous mixture which is free of solid masses is obtained.

Experimental Studies for Evaluation of the Physical Stability

On the purpose of demonstrating stability of the formulation to be improved when it contains the combination of *Hedera helix* extract and *Pelargonium sidoides* extract, firstly, three formulations are prepared according to the present invention. These formulations comprise:
Formulation 1: *Hedera helix* extract+excipients
Formulation 2: *Pelargonium sidoides* extract+excipients
Formulation 3: *Hedera helix* extract & *Pelargonium sidoides* extract+excipients Each of the above formulations prepared for the comparative experimental analysis comprises same excipients in the same amounts.

Examining changes in physical properties such as pH, density, viscosity, color, precipitation, taste, smell, etc of the formulations under stress conditions is useful in evaluating the physical stability of the formulations. Therefore, stress testing is carried out on the above formulations in an drying-oven at the temperature of 50° C. as a thermal condition and under conditions defined in ICH Q1B Photostability Testing of New Drug Substances and Products to determine the physical changes of the formulations. At specific time periods, physical analyses of the formulations are performed. Suprisingly, it has found that the formulation comprising the combination of *Hedera helix* extract and *Pelargonium sidoides* extract is the most stable formulation among the formulations that are analysed. Comparative results obtained at the end of the stress testing are given below:

Thermal Stress Testing

Thermal stress testing is carried out on the above formulations that are kept in a drying-oven with the temperature of 50° C. throughout 10 days. During testing period, the changes in the physical properties of the formulations are determined, and comparative results obtained at the end of the testing period are given below.

—pH

According to the comparative results of Table 1, the change in pH value of the Formulation 1 and Formulation 2 is higher than that of the Formulation 3 throughout the testing period. It shows that the pH value of the formulation comprising the combination of *Hedera helix* and *Pelargonium sioides* is more stable than that of the formulation comprising *Hedera helix* or *Pelargonium sidoides* alone. The increase occurred in the pH values of the Formulation 1 and the Formulation 2 also leads to the taste of the formulations to be changed throughout the testing period. Suprisingly, it has also found that while the pH value of the formulation approaches to 4, the taste of the formulation becomes better, thus, the Formulation 3 has the best taste among the formulations.

TABLE 1 pH values in the formulations versus time

| | 0 h | 5 h | 21 h | 29 h | 44 h | 54 h | 5 d | 6 d | 8 d | 9 d | 10 d |
|---|---|---|---|---|---|---|---|---|---|---|---|
| Formulation 1 | 4.27 | 4.35 | 4.36 | 4.38 | 4.41 | 4.39 | 4.43 | 4.45 | 4.52 | 4.55 | 4.62 |
| Formulation 2 | 4.79 | 4.90 | 4.87 | 4.90 | 5.04 | 5.12 | 5.16 | 5.13 | 5.18 | 5.24 | 5.32 |
| Formulation 3 | 4.16 | 4.15 | 4.17 | 4.15 | 4.12 | 4.15 | 4.15 | 4.14 | 4.16 | 4.18 | 4.25 | h: hour;
d: day

The pH values of the formulations throughout the testing period are measured using Mettler Toledo/Seven Multi pH meter at room temperature (25° C.±2° C.)

—Density

According to the comparative results of Table 2, the increase in density of the Formulation 1 and Formulation 2 is higher than that of the Formulation 3 throughout the testing period. As the same in the density of the formulations, the increase in the viscosity of the Formulation 1 and the Formulation 2 is higher than that of the Formulation 3 throughout the testing period that is shown in Table 3.

TABLE 2

Densities of the formulations versus time

| | 0 d | 10 d |
|---|---|---|
| Formulation 1 | 1.1289 g/mL | 1.1604 g/mL |
| Formulation 2 | 1.1268 g/mL | 1.1703 g/mL |
| Formulation 3 | 1.1315 g/mL | 1.1398 g/mL | d: day

TABLE 3

Viscosities of the formulations versus time

| | 0 d | 10 d |
|---|---|---|
| Formulation 1 | 19.2 mP | 22.1 mP |
| Formulation 2 | 20.1 mP | 22.7 mP |
| Formulation 3 | 21.1 mP | 21.5 mP | d: day

The densities of the formulations throughout the testing period are measured using Mettler Toledo DE40 density meter at room temperature (25° C.±2° C.) and the viscosities of the formulations throughout the testing period are measured using BROOKFIELD DV-II+Pro viscosity meter at room temperature (25° C.±2° C.).

—Precipitation

As shown in Table 4, although the precipitation is observed in the formulation comprising *Hedera helix* alone (Formulation 1), the addition of *Pelargonium sidoides* to the formulation comprising *Hedera helix* prevents the precipitation and provides the Formulation 3 to have a clear appearance and to maintain this clarity throughout the testing period.

TABLE 4

Precipitation in the formulations versus time

| | 0 h | 5 h | 21 h | 29 h | 44 h | 54 h | 5 d | 6 d | 8 d | 9 d | 10 d |
|---|---|---|---|---|---|---|---|---|---|---|---|
| Formulation 1 | + | + | + | + | + | + | + | + | + | + | + |
| Formulation 2 | − | − | − | − | − | − | − | − | − | − | − |
| Formulation 3 | − | − | − | − | − | − | − | − | − | − | − | h: hour;
d: day

This physical analysis to determine whether the precipitation is occurred or not in the formulations throughout the testing period, is performed by same analyst. Additionally, the analysis of each formulation is performed on the same ground which is a white flat ground lightened with a flash light parallel to the ground.

—Color

As shown in Table 5, although the color change is observed in the formulation comprising *Hedera helix* or *Pelargonium sidoides* alone (Formulation 1 or 2), any color change is not observed in the formulation comprising the combination of *Pelargonium sidoides* and *Hedera helix* (Formulation 3) throughout the testing period.

TABLE 5

Color change in the formulations versus time

| | 0 h | 5 h | 21 h | 29 h | 44 h | 54 h | 5 d | 6 d | 8 d | 9 d | 10 d |
|---|---|---|---|---|---|---|---|---|---|---|---|
| Formulation 1 | light brown | light brown | light brown | light brown | light brown | yellow | yellow | yellow | yellow | yellow | yellow |

TABLE 5-continued

| | Color change in the formulations versus time | | | | | | | | | | |
|---|---|---|---|---|---|---|---|---|---|---|---|
| | 0 h | 5 h | 21 h | 29 h | 44 h | 54 h | 5 d | 6 d | 8 d | 9 d | 10 d |
| Formulation 2 | yellow | yellow | yellow | yellow | yellow | light yellow | light yellow | light yellow | light yellow | light yellow | light yellow |
| Formulation 3 | brown | brown | brown | brown | brown | brown | brown | brown | brown | brown | brown | h: hour;
d: day

This physical analysis to determine whether the precipitation is occurred or not in the formulations throughout the testing period, is performed by same analyst. Additionally, the analysis of each formulation is performed on the same ground which is a white flat ground lightened with a flash light parallel to the ground, and the color of the formulations is decided using a color scale.

—Smell

It is observed that the smell of the Formulation 3 does not change whereas the smell of the other formulations change throughout the testing period. This physical analysis is also performed by same analyst in the same odorless environment for each formulation.

According to the thermal stress testing results, although the temperature at which the physical analyses are performed is high (50° C.), the Formulation 3 is less affected from the temperature in comparison with the other formulations, and thus, the physical stability of the Formulation 3 remains stable throughout the testing period.

Photostability Stress Testing

For determining the photostability of the formulations, the photostability stress testing is carried out under conditions defined in ICH Q1B Photostability Testing of New Drug Substances and Products. Two different conditions defined in the guideline are used during the testing period: initially formulations are kept in a photostability cabine with 200 Wh/m$^2$ at a constant temperature (25° C.) during 4 hours (ICH parameter-1). After the physical analyses of the formulations are carried out, these formulations are kept in a photostability cabine with 1.2 million lux hours at a constant temperature (25° C.) during 10 hours (ICH parameter-1).

According to the comparative results shown in Table 6, the Formulation 3 is the most photostable formulation among the formulations. The Formulation 3 is less affected from the light stress in comparison with other formulations, and thus the change in the physical properties of the Formulation 3 is less than that of the Formulation 1 and Formulation 2 at the end of the testing periods.

Consequently, these comparative results given from Table 1 to Table 6 demonstrate that the physical stability of the formulation comprising the combination of *Hedera helix* and *Pelargonium sidoides* (Formulation 3) is higher than that of the formulations comprising *Hedera helix* (Formulation 1) or *Pelargonium sidoides* (Formulation 2) alone. In other words, the addition of *Pelargonium sidoides* to the formulation comprising *Hedera helix* alone increases substantially the physical stability of the formulation comprising *Hedera helix*. Additionally, the fact that the Formulation 3 has an improved physical stability is also an indication of having an improved chemical stability.

The present invention shall be described further in the following examples. These examples are not intended to limit the scope of the present invention and are to be considered under the light of the foregoing detailed description.

Example 1

Solvents are stirred in a mixer until a homogeneous mixture is obtained. Then, inactive ingredients are added and are stirred until a homogeneous mixture is obtained. Finally, *Hedera helix* extract and *Pelargonium sidoides* extract are added respectively and are stirred until a homogeneous mixture is obtained. The resulting mixture is subjected to filtration and is let to settle. Following the settling period, the resulting final product is filled into suitable bottles.

| Ingredients | Quantity, % |
|---|---|
| *Pelargonium sidoides* extract | 0.2%-15% |
| *Hedera helix* extract | 0.25%-10% |
| Propylene glycol | 1%-60% |
| Glycerin | 25%-50% |
| Citric acid monohydrate | 0.01%-1% |

TABLE 6

| | Photostability of the formulations | | | | | | | |
|---|---|---|---|---|---|---|---|---|
| | ICH parameter -1 | | | | ICH parameter -2 | | | |
| | pH | Density (g/mL) | Precipitation | Color | pH | Density (g/mL) | Precipitation | Color |
| Formulation 1 | 4.39 | 1.1292 | + | light brown | 4.51 | 1.1396 | + | light yellow |
| Formulation 2 | 4.89 | 1.1276 | − | light yellow | 5.07 | 1.1274 | − | light yellow |
| Formulation 3 | 4.19 | 1.1316 | − | brown | 4.25 | 1.1312 | − | brown |

-continued

| Ingredients | Quantity, % |
| --- | --- |
| Sodium citrate dihydrate | 0.005%-0.5% |
| Sorbitol | 1%-60% |
| Sucralose | 0.01%-2% |
| Ammonium glycyrrhizinate | 0.01%-10% |
| Ethanol | 0.5%-30% |
| *Eucalyptus* | 0.01%-5% |
| Water | q.s. | q.s.: Sufficient quantity (to make up the total volume of the formulation to 100 ml).

Example 2

Solvents are stirred in a mixer until a homogeneous mixture is obtained. Then, inactive ingredients are added and are stirred until a homogeneous mixture is obtained. Finally, *Hedera helix* extract and *Pelargonium sidoides* extract are added respectively and are stirred at high speed until a homogeneous mixture is obtained. The resulting mixture is subjected to filtration and is let to settle. Following the settling period, the resulting final product is filled into suitable bottles.

| Ingredients | Quantity, % |
| --- | --- |
| *Pelargonium sidoides* extract | 0.1%-20% |
| *Hedera helix* extract | 0.1%-15% |
| Propylene glycol | 1%-60% |
| Glycerin | 25%-50% |
| Citric acid monohydrate | 0.03%-0.2% |
| Sodium citrate dihydrate | 0.015%-0.1% |
| Sorbitol | 10%-25% |
| Sucralose | 0.01%-2% |
| Ammonium glycyrrhizinate | 0.01%-10% |
| Ethanol | 0.5%-30% |
| *Eucalyptus* | 0.05%-2% |
| Water | q.s. | q.s.: Sufficient quantity (to make up the total volume of the formulation to 100 ml).

Example 3

Solvents are stirred in a mixer until a homogeneous mixture is obtained. Then, inactive ingredients are added and are stirred until a homogeneous mixture is obtained. Finally, *Hedera helix* extract, *Pelargonium sidoides* extract, and *Glycyrrhiza glabra* extract are respectively added and are stirred at high speed until a homogeneous mixture is obtained. The resulting mixture is subjected to filtration and is let to settle. Following the settling period, the resulting final product is filled into suitable bottles.

| Ingredients | Quantity, % |
| --- | --- |
| *Pelargonium sidoides* extract | 0.05%-30% |
| *Glycyrrhiza glabra* extract | 0.01%-90% |
| *Hedera helix* extract | 0.05%-20% |
| Propylene glycol | 1%-60% |
| Glycerin | 25%-50% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycyrrhizinate | 0.01%-10% |
| Ethanol | 0.5%-30% |

-continued

| Ingredients | Quantity, % |
| --- | --- |
| *Eucalyptus* | 0.01%-5% |
| Water | q.s. | q.s.: Sufficient quantity (to make up the total volume of the formulation to 100 ml).

Example 4

Solvents are stirred in a mixer until a homogeneous mixture is obtained. Then, inactive ingredients are added and are stirred until a homogeneous mixture is obtained. Finally, *Hedera helix* extract, *Pelargonium sidoides* extract, and Propolis extract are respectively added and are stirred at high speed until a homogeneous mixture is obtained. The resulting mixture is subjected to filtration and is let to settle. Following the settling period, the resulting final product is filled into suitable bottles.

| Ingredients | Quantity, % |
| --- | --- |
| *Pelargonium sidoides* extract | 0.2%-15% |
| Propolis extract | 0.05%-95% |
| *Hedera helix* extract | 0.25%-10% |
| Propylene glycol | 1%-60% |
| Glycerin | 25%-50% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycyrrhizinate | 0.01%-10% |
| Ethanol | 0.5%-30% |
| *Eucalyptus* | 0.01%-5% |
| Water | q.s. | q.s.: Sufficient quantity (to make up the total volume of the formulation to 100 ml).

Example 5

Solvents are stirred in a mixer until a homogeneous mixture is obtained. Then, inactive ingredients are added and are stirred until a homogeneous mixture is obtained. Finally, *Hedera helix* extract, *Pelargonium sidoides* extract, Propolis extract and *Glycyrrhiza glabra* extract are respectively added and are stirred at high speed until a homogeneous mixture is obtained. The resulting mixture is subjected to filtration and is let to settle. Following the settling period, the resulting final product is filled into suitable bottles.

| Ingredients | Quantity, % |
| --- | --- |
| *Pelargonium sidoides* extract | 0.2%-15% |
| *Glycyrrhiza glabra* extract | 0.01%-90% |
| Propolis extract | 0.05%-95% |
| *Hedera helix* extract | 0.25%-10% |
| Propylene glycol | 1%-60% |
| Glycerin | 25%-50% |
| Citric acid monohydrate | 0.01%-1% |
| Sodium citrate dihydrate | 0.005%-0.5% |
| Sorbitol | 1%-60% |
| Sucralose | 0.01%-2% |
| Ammonium glycyrrhizinate | 0.01%-10% |
| Ethanol | 0.5%-30% |
| *Eucalyptus* | 0.01%-5% |
| Water | q.s. | q.s.: Sufficient quantity (to make up the total volume of the formulation to 100 ml).

The invention claimed is:

1. A formulation comprising effective amounts of *Hedera helix* extract and *Pelargonium sidoides* extract, wherein the percentage amount of the *Hedera helix* extract is between 0.05% and 20% (w/v), based on the total volume of the formulation, and the percentage amount of *Pelargonium sioides* extract is between 0.05% and 30% (w/v), based on the total volume of the formulation.

2. The formulation according to claim 1, wherein the ratio of the *Hedera helix* extract to the *Pelargonium sidoides* extract is between 1:0.1 and 1:45.

3. The formulation according to claim 1, wherein said formulation is administered by an oral, parenteral, ocular, nasal, buccal, sublingual, or topical route.

4. The formulation according to claim 1 further comprising at least one excipient.

5. The formulation according to claim 4, wherein said at least one excipient is a pharmaceutically acceptable excipient selected from the group consisting of fillers, solvents, pH regulating agents, sweeteners, aromatic agents and preservatives; or said formulation comprises each of the following pharmaceutically acceptable excipients: a filler, a solvent, a pH regulating agent, a sweetener, and an aromatic agent, and, optionally a preservative.

6. The formulation according to claim 5, wherein:
   (a) the formulation comprises no preservative;
   (b) the aromatic agent is selected from the group consisting of fruit aromas selected from orange, cherry, strawberry, banana, sourcherry, lemon; aromas of cardamom, anis, mint, menthol, *eucalyptus*, vanillin, and ethyl vanillin, and mixtures thereof;
   (c) the aromatic agent is *eucalyptus* and the percentage amount of *eucalyptus* is between 0.01% and 5% (w/v), based on the total volume of the formulation; or
   (d) the sweetener is selected from the group consisting of sucralose, ammonium glycyrrhizinate, acesulfame-K, aspartame, saccharine or sodium and calcium salts of saccharine, sodium cyclamate, sucrose, fructose, glucose, sorbitol and mixtures thereof, and optionally wherein the percentage amount of the sweetener is between 0.005% and 20% (w/v), based on the total volume of the formulation.

7. The formulation according to claim 1, wherein the percentage amount of the *Hedera helix* extract is between 0.1% and 15% (w/v), based on the total volume of the formulation.

8. The formulation according to claim 7, wherein the percentage amount of the *Hedera helix* extract is between 0.25% and 10% (w/v), based on the total volume of the formulation.

9. The formulation according to claim 1, wherein the percentage amount of the *Pelargonium sioides* extract is between 0.1% and 20% (w/v), based on the total volume of the formulation.

10. The formulation according to claim 9, wherein the percentage amount of the *Pelargonium sioides* extract is between 0.2% and 15% (w/v), based on the total volume of the formulation.

11. The formulation according to claim 2, wherein the ratio of the *Hedera helix* extract to the *Pelargonium sidoides* extract is between 1:0.25 and 1:25.

12. The formulation according to claim 11, wherein the ratio of the *Hedera helix* extract to the *Pelargonium sidoides* extract is between 1:0.5 and 1:15.

13. The formulation according to claim 1, comprising the following:

a. 0.05% to 20% by weight of *Hedera helix* extract,
   b. 0.05% to 30% by weight of *Pelargonium sidoides* extract,
   c. 1% to 60% by weight of propylene glycol,
   d. 25% to 50% by weight of glycerin,
   e. 0.01% to 1% by weight of citric acid monohydrate,
   f. 0.005% to 0.5% by weight of sodium citrate dihydrate,
   g. 1% to 60% by weight of sorbitol,
   h. 0.01% to 2% by weight of sucralose,
   i. 0.01% to 10% by weight of ammonium glycyrrhizinate,
   j. 0.5% to 30% by weight of ethanol, and
   k. 0.01% to 5% by weight of *eucalyptus*;
or
   a. 0.25% to 10% by weight of *Hedera helix* extract,
   b. 0.2% to 15% by weight of *Pelargonium sidoides* extract,
   c. 10% to 30% by weight of propylene glycol,
   d. 25% to 50% by weight of glycerin,
   e. 0.03% to 0.2% by weight of citric acid monohydrate,
   f. 0.015% to 0.1% by weight of sodium citrate dihydrate,
   g. 10% to 25% by weight of sorbitol,
   h. 0.01% to 2% by weight of sucralose,
   i. 0.01% to 10% by weight of ammonium glycyrrhizinate,
   j. 0.5% to 30% by weight of ethanol, and
   k. 0.05% to 2% by weight of *eucalyptus*.

14. The formulation according to claim 1, comprising a therapeutically effective amount of an extract of *Hedera helix*, wherein the extract further comprises an extract of *Pelargonium sioides* in an amount effective to improve the physical stability of the formulation.

15. The formulation according to claim 14, wherein the improved physical stability is characterized by a feature selected from the group consisting of maintenance of pH value, maintenance of density, maintenance of viscosity, reduction in precipitation, maintenance of color, maintenance of smell, and maintenance of photostabillty.

16. The formulation according to claim 5, wherein the filler is selected from the group consisting of sucrose, sorbitol, xylitol, dextrose, fructose, maltitole, sugar potassium, aspartame, saccharine, saccharine sodium, spray dried or anhydrous lactose, mannitol, starch, cellulose and mixtures thereof, and wherein when the filler is sorbitol, the percentage amount of sorbitol is optionally between 1% and 60% (w/v), based on the total volume of the formulation.

17. The formulation according to claim 5, wherein the pH regulating agent is selected from the group consisting of ascorbic acid, acetic acid, tartaric acid, citric acid, sodium citrate, citric acid and sodium citrate, potassium citrate, sodium phosphate, tricalcium phosphate, calcium carbonate, sodium bicarbonate, calcium phosphates, carbonated calcium phosphates, magnesium hydroxide, and hydrates thereof, and mixtures thereof, and wherein when the pH regulating agent is citric acid monohydrate and sodium citrate dehydrate, the weight ratio of sodium citrate dihydrate to citric acid monohydrate is optionally 1:2, and optionally the percentage amount of citric acid monohydrate in the formulation is between 0.01% and 1% (w/v), based on the total volume of the formulation, whereas the percentage amount of sodium citrate dihydrate is between 0.005% and 0.5% (w/v), based on the total volume of the formulation.

18. The formulation according to claim 5, wherein the solvent is selected from the group consisting of a combination of propylene glycol, glycerin, water, and ethanol; propylene glycol, glycerin, water, ethanol, isopropyl alcohol and similar water-soluble polar and water-insoluble non-polar solvents or a mixture thereof, and optionally wherein the solvent is in a quantity of at least 5%.

19. A method for preparing a formulation according to claim 1, comprising the following steps:
   a. adding all solvents to a container where production is to be made and stirring the resulting mixture until a homogeneous mixture is obtained (mixture A),
   b. adding inactive ingredients to the container containing the mixture A and stirring the resulting mixture until a homogeneous mixture is obtained (mixture B),
   c. adding *Hedera helix* extract and *Pelargonium sidoides* extract, which are the herbal active agents, respectively to mixture B obtained in the preceding step and stirring the resulting mixture until a homogeneous mixture is obtained (mixture C),
   d. converting the mixture C obtained into a suitable dosage form and filling into packages, or subjecting mixture C to filtration, allowing it to settle, and filling the resulting product into suitable bottles.

20. A method of treating or preventing a respiratory tract disease in a subject, or alleviating or eliminating a symptom thereof, the method comprising administering a formulation of claim 1 to the subject.

* * * * *